United States Patent
Chi et al.

(10) Patent No.: US 11,382,878 B2
(45) Date of Patent: Jul. 12, 2022

(54) USE OF METFORMIN AND SODIUM BUTYRATE FOR TREATING CONDITIONS INDUCED BY CHRONIC INFLAMMATION

(71) Applicant: Johnpro Biotech Inc., Taipei (TW)

(72) Inventors: Kwan-Hwa Chi, Taipei (TW); Yu-Shan Wang, Taipei (TW); Hsin-Chien Chiang, Taipei (TW); Kai-Chung Cheng, Taipei (TW)

(73) Assignee: JOHNPRO BIOTECH INC., Taipei (TW)

( * ) Notice: Subject to any disclaimer, the term of this patent is extended or adjusted under 35 U.S.C. 154(b) by 5 days.

(21) Appl. No.: 16/618,161

(22) PCT Filed: May 31, 2017

(86) PCT No.: PCT/CN2017/086658
§ 371 (c)(1),
(2) Date: Nov. 29, 2019

(87) PCT Pub. No.: WO2018/218521
PCT Pub. Date: Dec. 6, 2018

(65) Prior Publication Data
US 2021/0015769 A1      Jan. 21, 2021

(51) Int. Cl.
| | | |
|---|---|---|
| *A61K 31/155* | (2006.01) | |
| *A61K 31/19* | (2006.01) | |
| *A61P 29/00* | (2006.01) | |
| *A61P 17/02* | (2006.01) | |
| *A61P 17/16* | (2006.01) | |
| *A61K 9/00* | (2006.01) | |

(52) U.S. Cl.
CPC .......... *A61K 31/155* (2013.01); *A61K 9/0014* (2013.01); *A61K 9/0019* (2013.01); *A61K 9/0031* (2013.01); *A61K 31/19* (2013.01); *A61P 17/02* (2018.01); *A61P 29/00* (2018.01)

(58) Field of Classification Search
CPC ....... A61K 31/155; A61K 31/19; A61P 17/02; A61P 17/16; A61P 29/00
See application file for complete search history.

(56) References Cited

U.S. PATENT DOCUMENTS

| | | | |
|---|---|---|---|
| 9,532,960 B2* | 1/2017 | Chi | .................. A61P 35/00 |
| 9,913,816 B2* | 3/2018 | Chi | .................. A61K 31/19 |
| 2014/0343144 A1* | 11/2014 | Chi | .................. A61P 35/00 |
| | | | 514/557 |
| 2017/0071887 A1 | 3/2017 | Chi et al. | |
| 2017/0165214 A1* | 6/2017 | Cahan | .................. A61K 9/4816 |

OTHER PUBLICATIONS

Kanterman et al. Seminars in Cancer Biology 2012, 22, 307-318.*
Multhoff et al. Frontiers in Immunology 2012, published Jan. 12, 2012, Article 98, pp. 1-17.*
Meira et al. J Clin Invest 2008, 118 (7), 2516-2525.*
Vernia et al. Lancet 2000, 356, 1232-1235.*
Canani et al. World J Gastropenterol 2011, 17 (12), 1519-1528.*
Saisho, M. Endocrine, Metabolic & Immune Disorders—Drug Targets 2015, 15, 196-205.*
Terzic et al. Gastroenterology 2010, 138, 2101-2114.*
Zheng et al. Biomedicine & Pharmacotherapy 2020, 131, 110664.*
DiCarlo et al. Radiat Res 2020, 194 (3), 315-344.*
Citrinetai. Radiat Res 2017, 188 (1), 1-20.*
Diaz et al., "Metformin improves in vivo and in vitro B cell function in individuals with obesity and Type-2 Diabetes", Elsevier, 2017.
Zhang et al., "Research progress on the mechanism of butyrate ininflammatory reaction", CNKI, 2015.
Stojcev et al., "Early treatment and prevention of the radiation proctitis—composite enemas containing sodium butyrate", Springer, Mar. 21, 2013.
Miller et al., "Metformin Exhibits Radiation Countermeasures Efficacy When Used Alone or in Combination with Sulfhydryl Containing Drugs", Radiation Research Society, 2014, pp. 464-470.

* cited by examiner

*Primary Examiner* — Irina Neagu

(57) ABSTRACT

Disclosed herein are compositions and methods for the treatment of conditions induced by chronic inflammation. According to some embodiments, the compositions and methods involve the use of metformin and sodium butyrate in the treatment of conditions induced by chronic inflammation.

11 Claims, 9 Drawing Sheets

Non-radiation (NC)  Mouse A

Mouse B  Mouse C

Mouse A

Mouse B

Mouse C

Mouse A  Mouse B

Healthy control

Cortisone

Saline

Metformin/NaB_1

Metformin/NaB_2

USE OF METFORMIN AND SODIUM BUTYRATE FOR TREATING CONDITIONS INDUCED BY CHRONIC INFLAMMATION

CROSS-REFERENCE TO RELATED APPLICATION

This application is a U.S. National Stage Filing under 35 U.S.C. 371 from International Patent Application Serial No. PCT/CN2017/086658, entitled "USE OF METFORMIN AND SODIUM BUTYRATE FOR TREATING CONDITIONS INDUCED BY CHRONIC INFLAMMATION," filed on May 31, 2017, and published on Dec. 6, 2018, the disclosure of which are incorporated by reference herein in their entireties.

BACKGROUND OF THE INVENTION

The present disclosure relates to compositions and methods for the treatment of conditions induced by chronic inflammation. More particularly, the present compositions and methods involve the use of metformin and sodium butyrate in the treatment of conditions induced by chronic inflammation.

DESCRIPTION OF RELATED ART

Radiation therapy has been used in the treatment of a wide variety of clinical settings as either adjuvant, neoadjuvant, primary, definitive, or palliative treatment for subjects with cancer. In spite of the efforts taken by the radiation oncologists carrying out the radiation treatment, significant radiation-induced injury remains a common side effect. For example, patients receiving abdominopelvic radio therapies often suffer from radiation induced proctosigmoiditis, enteritis, proctitis, and/or cystitis.

Symptoms of radiation induced conditions are quite variable; they may occur weeks to years after the radiation exposure. Acute radiation-induced proctitis is the most relevant radiation induced side effect for pelvic cancer. According to statistics, it occurs in approximately 75% of patients receiving pelvic radiation and results in bleeding, pain, abdominal cramping, mucoid discharge, and faecal urgency. Usually, the acute symptoms will resolve within a few months upon the cessation of irradiation, but approximately 20% of patients may develop a chronic condition.

Several drugs, including corticosteroids, or nonsteroidal anti-inflammatory agents, have been used to reduce the acute mucosal reaction caused by radiation. But treatment of acute or chronic radiation induced proctitis, as well as other radiation induced conditions remains unsatisfactory.

Periodontal disease refers to any inflammation disease of the tissue surrounding the tooth, i.e., periodontium. Chronic inflammatory periodontal disease (CIPD) is the major cause of tooth loss in adults. Various attempts have been made to treat CIPD, such as the use of compositions containing antimicrobial compounds or various non-steroidal anti-inflammatory agents (NSAIDs). Nonetheless, the current treatment regimens are not effective in combating periodontal diseases.

In many cases, chronic inflammation also causes wounds at the inflammation site, and these wounds would not heal due to the continued inflammation at the wounds.

In view of the foregoing, there exists a need in the art for providing a novel medicament and method for treating conditions induced by chronic inflammation, such as those caused by radiation therapy or periodontal disease.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a method for treating one or more conditions induced by chronic inflammation in a subject in need of such treatment.

According to some embodiments of the present disclosure, the method comprises the step of administering to the subject an effective amount of metformin and an effective amount of sodium butyrate.

In some embodiments, the effective amount of metformin is 1 to 40 grams per day; preferably, the effective amount is 5 to 10 grams per day.

In some embodiments, the effective amount of sodium butyrate is 0.1 to 4 grams per day; preferably, the effective amount is 0.5 to 1 grams per day.

According to various embodiments of the present disclosure, the metformin and sodium butyrate are administered to the subject once, twice or three times a day. In some embodiments, the metformin and sodium butyrate are administered concurrently, while in some other embodiments, the two are administered separately. Regarding the mode of administration, the metformin and sodium butyrate may be administered topically, rectally, enterally, or via injection, infusion or catheter delivery.

In some optional embodiments, the metformin and sodium butyrate are formulated in a single pharmaceutical composition. Alternatively, the metformin and sodium butyrate are formulated in two separate pharmaceutical compositions.

According to embodiments of the present disclosure, the chronic inflammation condition therapy is caused by the radiation therapy. For example, the radiation induced condition is radiation proctitis, radiation enteritis, radiation proctosigmoiditis, radiation induced ulcers, radiation cystitis, radiation necrosis, radiation proctocolitis, radiation dermatitis, radiation burns, radiation dermatitis, injury and atrophy to respiratory epithelia, radiation induced fibrosis in tissues, radiation mucositis in the alimentary canal, radiation osteonecrosis, or radiation induced arterial stenosis.

In some other cases, the conditions induced by the radiation therapy is caused by periodontal disease, such as chronic inflammatory periodontal disease.

In certain embodiments, the condition caused by chronic inflammation includes wounds at the inflammation site.

In still another aspect, the present disclosure is directed to a pharmaceutical composition or kit for treating one or more conditions induced by chronic inflammation in a subject in need of such treatment.

According to some embodiments, the pharmaceutical composition comprises an effective amount of metformin, an effective amount of sodium butyrate, and a pharmaceutically acceptable excipient.

According to other embodiments, the pharmaceutical kit comprises two separate pharmaceutical compositions. The first pharmaceutical composition comprises an effective amount of metformin and a first pharmaceutically acceptable excipient, whereas the second pharmaceutical composition comprises an effective amount of sodium butyrate and a second pharmaceutically acceptable excipient. The first and second pharmaceutically acceptable excipient may be the same or different.

Subject matters that are also included in other aspects of the present disclosure include the use of metformin and sodium butyrate in the manufacture of a medicament for use in the treatment of one or more conditions induced by chronic inflammation, as well as metformin and sodium butyrate for use in the treatment of one or more conditions induced by chronic inflammation.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

Figure 1:
FIG. 1 provides representative photographs illustrating the appearance of mice before radiation according to Example 1 of the present disclosure.
Figure 1:
Figure 1:
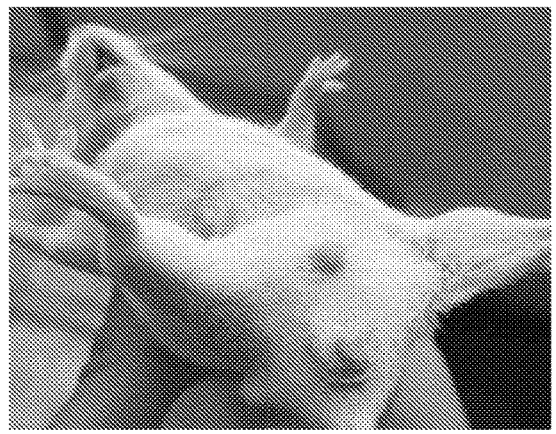
Figure 1:

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

The terms "treatment" and "treating" as used herein may refer to a preventative (e.g., prophylactic), curative or palliative measure. In particular, the term "treating" as used herein refers to the application or administration of metformin and sodium butyrate or a pharmaceutical composition or kit comprising the same to a subject, who has a medical condition, a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The terms "subject" and "patient" are used interchangeably herein and are intended to mean an animal including the human species that is treatable by the metformin and sodium butyrate, pharmaceutical composition, and/or method of the present invention. The term "subject" or "patient" intended to refer to both the male and female gender unless one gender is specifically indicated.

The terms "application" and "administration" are used interchangeably herein to mean the application of metformin and sodium butyrate or a pharmaceutical composition or kit of the present invention to a subject in need of a treatment thereof, e.g., those suffer from one or more conditions induced by chronic inflammation.

The term "effective amount" as used herein refers to the respective quantity of the metformin and sodium butyrate that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, as the total mass of ester prodrug (e.g., in grams, milligrams or micrograms) or a ratio of mass of ester prodrug to body mass, e.g., as milligrams per kilogram (mg/kg).

The phrase "pharmaceutically acceptable excipient" as used herein means a pharmaceutically acceptable material, composition or vehicle, such as a liquid or solid filler, diluent, carrier, solvent or encapsulating material, involved in carrying or transporting the subject agents to the desired organ or portion of the patient's body. Each excipient must be "acceptable" in the sense of being compatible with the other ingredients of the formulation. The pharmaceutical formulation contains a compound of the invention in combination with one or more pharmaceutically acceptable ingredients. The excipient can be in the form of a solid, semi-solid or liquid diluent, cream or a capsule. These pharmaceutical preparations are a further object of the invention. Usually, the amount of active compound is between 0.1-95% by weight of the preparation, preferably between 0.2-20% by weight in preparations for parenteral use, and preferably between 1 and 50% by weight in preparations for oral administration. For the clinical use of the methods of the present invention, the pharmaceutical composition of the invention is formulated into formulations suitable for the intended route of administration.

The present disclosure is based, at least in part, on the discovery that the combination of metformin and sodium butyrate synergistically ameliorate the condition(s) caused by chronic inflammation in the patient. In view of the foregoing, the present disclosure proposes methods for treating condition(s) caused by the radiation therapy. Some embodiments of the present disclosure are directed to methods for treating disorders caused by the radiation therapy. Also provided herein is the use of metformin and sodium butyrate in the above-mentioned treatment, as well as for use in the manufacture of a medicament for said treatment purpose. The medicament (i.e., a pharmaceutical composition or a pharmaceutical kit) is, of course, a subject matter covered by the scope of the present application.

In one aspect, the present disclosure is directed to a method for treating one or more conditions induced by chronic inflammation in a subject in need of such treatment.

According to some embodiments of the present disclosure, the method comprises the step of administering to the subject an effective amount of metformin and an effective amount of sodium butyrate.

In some embodiments, the effective amount of metformin is about 1 to 40 grams per day; preferably, the effective amount is about 5 to 10 grams per day. For example, the effective amount of metformin is about 1, 1.5, 2, 2.5, 3, 3.5, 4, 4.5, 5, 5.5, 6, 6.5, 7, 7.5, 8, 8.5, 9, 9.5, 10, 15, 20, 25, 30, 35 or 40 grams per day for an adult human having a body weight in the range of about 40 to 80 kilograms.

In some embodiments, the effective amount of sodium butyrate is about 0.1 to 4 grams per day; preferably, the effective amount is about 0.5 to 1 grams per day. For example, the effective amount of sodium butyrate is about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, or 4 grams per day for an adult human having a body weight in the range of about 40 to 80 kilograms.

For example, the metformin and sodium butyrate can be formulated, together with a pharmaceutically acceptable excipient, into a single pharmaceutical composition suitable for the desired mode of administration. Alternatively, each of the metformin and sodium butyrate may be formulated with a respective pharmaceutically acceptable excipient, thereby giving two separate pharmaceutical compositions. As could be appreciated, in the latter case, the respective pharmaceutically acceptable excipient for metformin and sodium butyrate may the same or different.

The dosage form of the present pharmaceutical composition generally depends on the route of administration. According to various embodiments of the present disclosure, the metformin and sodium butyrate or the pharmaceutical composition comprising either or both of the two components may be administered topically, rectally, enterally, or via injection, infusion or catheter delivery.

Certain pharmaceutical compositions prepared in accordance with the presently disclosed and claimed inventive concept(s) are single unit dosage forms suitable for oral, mucosal (e.g., vaginal, buccal, or rectal), parenteral (e.g., subcutaneous, intravenous, bolus injection, intramuscular, or intraarterial), or transdermal administration to a patient. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; enema; gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. As could be appreciated, these pharmaceutical compositions are also within the scope of the present disclosure.

In various embodiments, the subject is a mammal, which may benefit from the treatment method of the present disclosure. As used herein, "mammal" refers to all members of the class Mammalia, including humans; primates (e.g., monkey and chimpanzee); domestic and farm animals, such as dog, cat, rabbit, pig, sheep, goat, cow, horse, and cattle; as well as zoo, sports or pet animals; and rodents, such as mouse, rat and guinea pig. In an exemplary embodiment, the patient is a human.

According to various embodiments of the present disclosure, the metformin and sodium butyrate are administered in one or more applications during the course of treatment. For example, according to various embodiments of the present disclosure, the metformin and sodium butyrate are administered to the subject every day, every other day, or on selected days during the course of treatment. Also, on the day that metformin and sodium butyrate are administered, the drugs may be given once, twice or three times a day. In some embodiments, the metformin and sodium butyrate are administered concurrently, while in some other embodiments, the two are administered separately.

In some cases, metformin is administered before or after each application of sodium butyrate. In other cases, metformin is administered concurrently with each application of the sodium butyrate; for example, metformin and sodium butyrate can be provided in a same dosage unit. It is also possible that metformin and sodium butyrate are given at different time interval; for example, one dose of metformin is given first, followed by two or more applications of sodium butyrate, and then a second dose of metformin can be given, and so on, and vise versa. Still alternatively, the first dose of metformin is administered concurrently with one dose of the sodium butyrate, followed by one or more doses of sodium butyrate alone, and then, a second dose of metformin is administered concurrently with another dose of sodium butyrate, and vice versa. When metformin and sodium butyrate are not administered concurrently, the time between the administration of the two may be at least 1, 2, 3, 4, 5, 6, 7, 8, 9, 10, 15, 20, 25, 30, 35, 40, 45, 50, or 55 minutes, or 1, 1.5, 2, 2.5, 3, 3.5, 4, 4.5, 5, 5.5, or 6 hours.

In some cases, the conditions caused by chronic inflammation include wounds at the inflammation site. According to embodiments of the present disclosure, the chronic inflammation condition therapy is caused by the radiation therapy or periodontal disease. Illustrative examples of the radiation induced condition include, radiation proctitis, radiation enteritis, radiation proctosigmoiditis, radiation induced ulcers, radiation cystitis, radiation necrosis, radiation proctocolitis, radiation dermatitis, radiation burns, radiation dermatitis, injury and atrophy to respiratory epithelia, radiation induced fibrosis in tissues, radiation mucositis in the alimentary canal, radiation osteonecrosis, and radiation induced arterial stenosis.

Yet another aspect of the present disclosure is directed to the use of metformin and sodium butyrate in in the manufacture of a medicament for use in the treatment of one or more conditions induced by chronic inflammation. Still another aspect of the present disclosure is direct to the use of metformin and sodium butyrate in the treatment of one or more conditions induced by chronic inflammation. As could be appreciated, the description regarding the effective amount, the formulation and dosage form of the pharmaceutical compositions according to various embodiments of the above-mentioned aspect of the present disclosure are also applicable in these aspects.

The following discussion is provided to elucidate certain aspects of the present invention and to aid those of skilled in the art in practicing this invention. This discussion is in no way to be considered to limit the scope of the invention in any manner. Without further elaboration, it is believed that one skilled in the art can, based on the description herein, utilize the present invention to its fullest extent.

EXAMPLES

Animals and Methods

The experiments were performed using 8-week-old male BALB/c mice. All animals were housed in an animal room under temperature control (24-25° C.) and 12:12 light-dark cycle.

Standard laboratory chow and tap water were available ad libitum. The experiments procedures were in compliance with national animal welfare regulations in Taiwan.

Ten mice were randomly assigned into the following treatment groups: control (without radiation), n=1; 0.5 mL saline, n=3; 0.5 mL cortisone, n=3; 1% metformin and 80 mM sodium butyrate (NaBu) in 0.5 mL cortisone, n=3. Each experiment was performed in duplicate.

The blood samples of the mice were collected the next day (Day 0) after arrivals of the animals. All mice, except those in the control group, were subjected to one round of radiation (30 Gy, brachytherapy, 1 cm) on Day 1. Mice in each group received respective treatments rectally via the enema, which were administered once daily from Day 8 to Day 14. Mice were sacrificed on Day 14, and rectum samples were harvested, fixed, sectioned and stained with hematoxylin and eosin (H&E) to evaluate the inflammation condition of the rectum tissue at the designated time points. For immunohistochemical staining, the samples were stained with Dab (anti-F4/80 antibody) and counterstained with methyl green (anti-MMP-2 antibody and anti-MMP-9 antibody).

Example 1

Pre-Test Investigation

During pre-test investigation, the anatomical observation was conducted to evaluate the effect of radiation on the rectum tissue. Mice were treated with 30 Gy radiation on Day 1. Photographs in FIG. 1 were taken before the radiation, whereas photographs in FIG. 2A and FIG. 3A were respectively taken on 7, and 13 days after the radiation to show the appearance at the radiation site. On the $7^{th}$ and $13^{th}$ day, mice C and B were sacrificed, and their rectum tissues were shown in FIG. 2B and FIG. 3B, respectively.

Figure 2A:
FIG. 2A provides representative photographs illustrating the appearance of mice that were treated with radiation (Mice A to C) on the Day 7 after radiation according to Example 1 of the present disclosure.
Figure 2A:
Figure 2A:
Figure 2B:
FIG. 2B provides representative photographs illustrating the rectum tissue of Mouse C on the Day 7 after radiation according to Example 1 of the present disclosure.
Figure 2B:
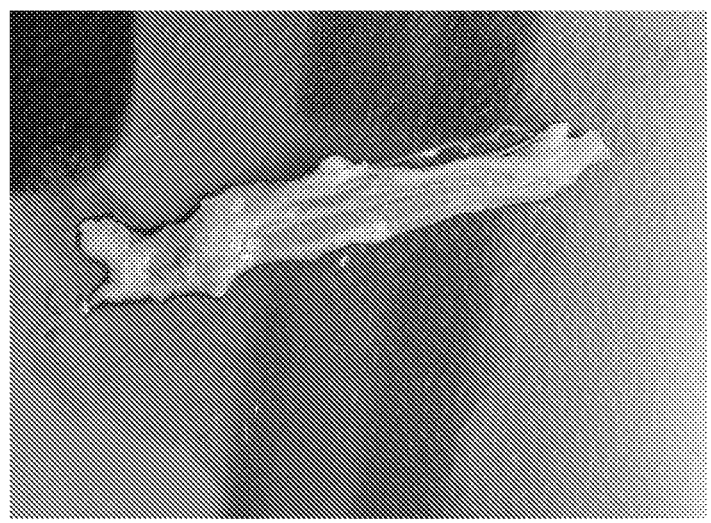
Figure 3A:
FIG. 3A provides representative photographs illustrating the appearance of mice that were treated with radiation (Mice A and B) on the Day 13 after radiation according to Example 1 of the present disclosure.
Figure 3A:
Figure 3B:
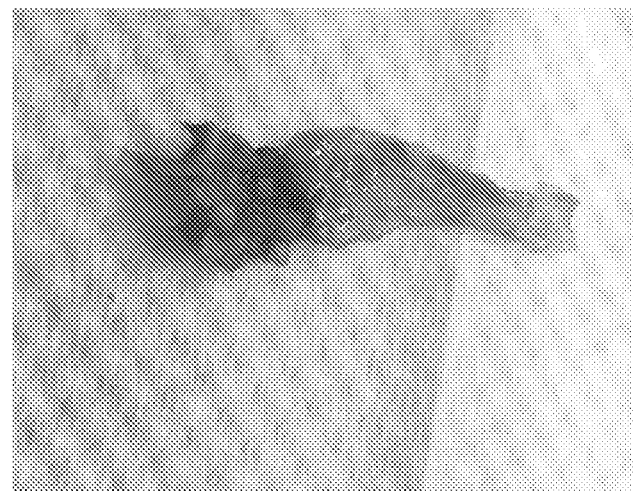
FIG. 3B provides representative photographs illustrating the rectum tissue of Mouse B on the Day 13 after radiation according to Example 1 of the present disclosure.

As could be seen in FIG. 1, before the radiation, the appearances of the tissue around the anus of the mice from the control group (NC) and experimental group (mice A to C) are normal. However, referring to FIG. 2A, after being radiated on Day 1, slight swelling was observed in the anal tissue of mice A to C on Day 7, and minor flushing and bleeding was seen from the anatomical examination of the rectum tissue from mice C, as shown in FIG. 2B. On 13 days after the radiation, the swelling of the anal tissue continued, and slightly loose stool was observer, possibly caused by mucosa damage (see, FIG. 3A). Also, in FIG. 3B, significant flushing and bleeding was observed in the rectum mucosa.

Example 2

Effect of Metformin and Sodium Butyrate on Radiation Induced Inflammation in Mice Mice were treated as described above in "Animals and Methods," and FIG. 4A and FIG. 4B are representative photographs of the rectum tissue from mice of each treatment group.

Figure 4A:
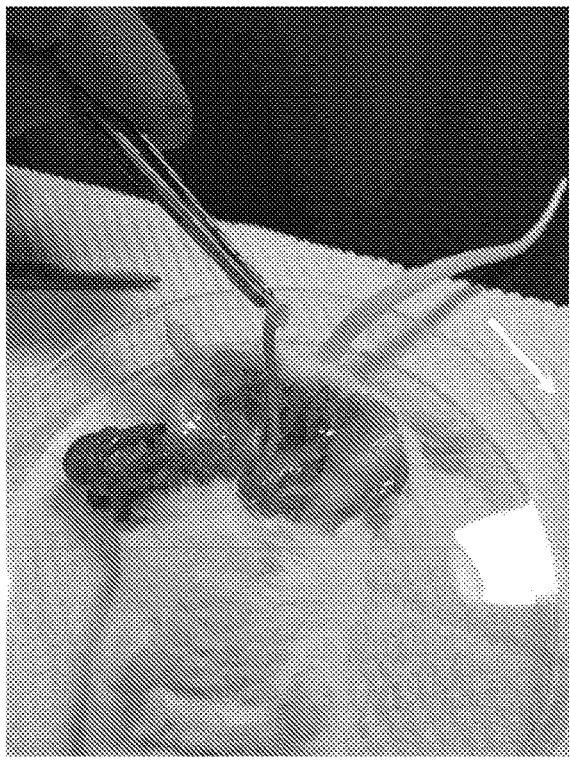
FIG. 4A and FIG. 4B provide representative photographs illustrating the rectum of mice of different treatment group on Day 14 after radiation according to Example 2 of the present disclosure.
Figure 4A:
Figure 4A:
Figure 4B:
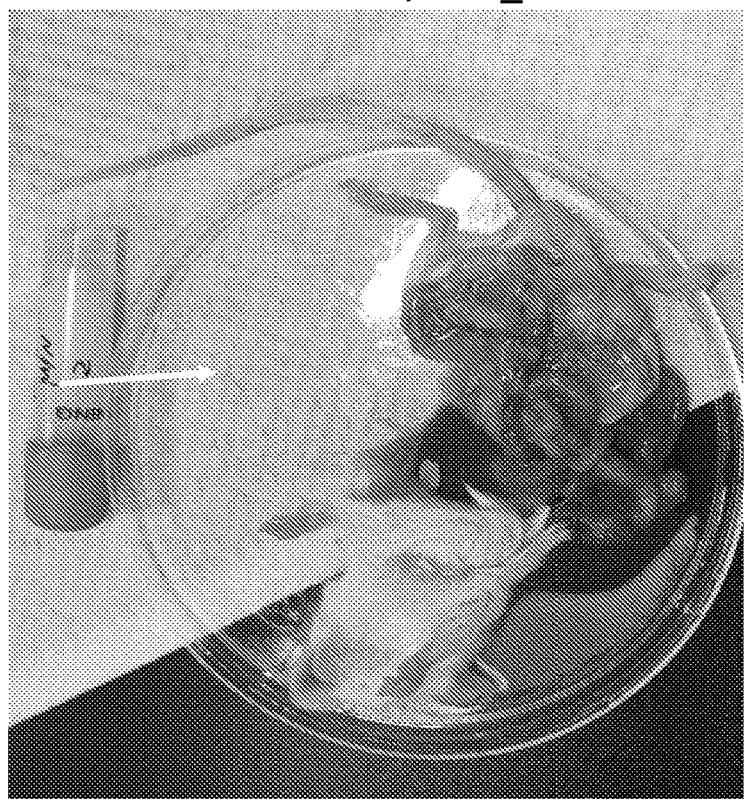
Figure 4B:

Reference is made to FIG. 4A, which is a representative photograph taken from the mice in the healthy control group (i.e., mice that were not subjected to radiation), which showed no sign of any rectum inflammation. On the other hand, for mice treated with cortisone or saline, a significant amount of loose stool was seen in the rectum, indicating that the rectum mucosa has lost its function of absorbing the water content in the stool. In contrast, referring to FIG. 4B, for mice treated with the present composition comprising metformin and sodium butyrate, stool particles were seen in the rectum, suggesting that the mucosa retained its physiological function despite the radiation.

Figure 5A:
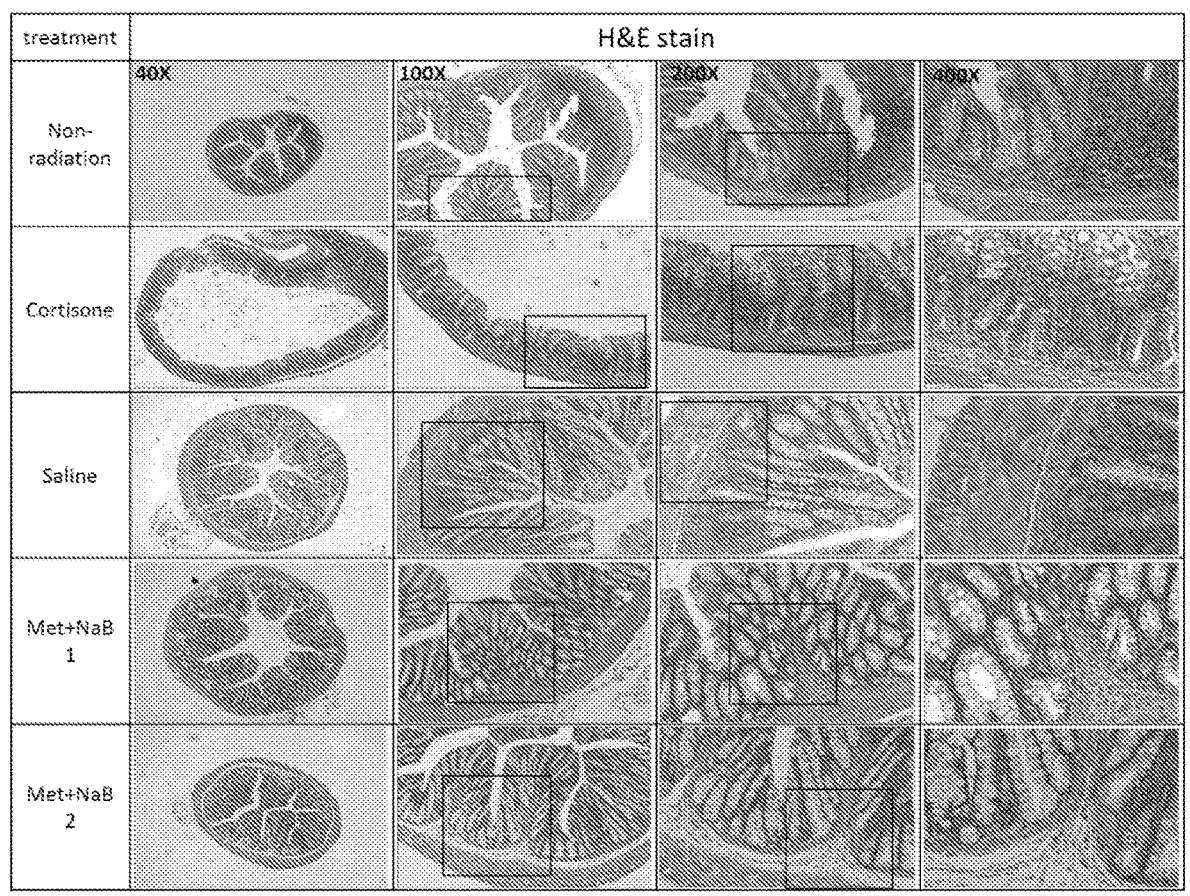
FIG. 5A shows the hematoxylin and eosin (H&E) staining results according to Example 2 of the present disclosure.

The H&E stains in FIG. 5A indicated that for mice treated with cortisone, the crypt tissue was not observed. In contrast, the crypt tissue was seen in the saline-treated mice; yet the integrity of the crypt tissue of the saline-treated mice is inferior to that of those treated with metformin/NaBu. These H & E stains indicated that the present metformin/NaBu treatment effectively reduce the damage to the intestine mucosa caused by the radiation.

Figure 5B:
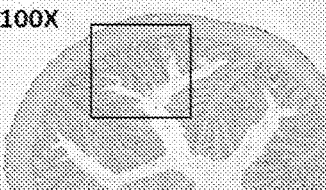
FIG. 5B and FIG. 5C show the immunohistochemical staining (methyl green and Dab) results according to Example 2 of the present disclosure.
Figure 5C:
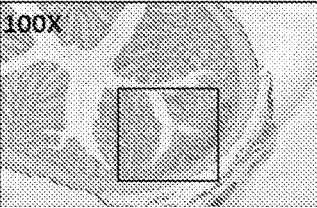

It is known that the over-expression of MMP2 and MMP9 may impede the wound healing. However, from the immunohistochemical staining results summarized in FIG. 5B and FIG. 5C, it is observed that the expression level of MMP2 and MMP9 in the metformin/NaBu-treated mice is lower than that of those treated with cortisone or saline.

The experimental data provided in this example evidenced that the proposed treatment with metformin and sodium butyrate effectively ameliorate the inflammation caused by radiation therapy in mice.

Example 3

Effect of Metformin and Sodium Butyrate on Radiation Proctitis

A 44-year old male patient suffered from anal squamous cell carcinoma at 3 to 7 o'clock of anal verge; an anal tumor (2.5-3 cm) above the dentate line with regional lymph node metastases; the patient was diagnosed with clinical staging of T2N3M0. He received the definitive concurrent chemo-radiotherapy (CCRT) to 55.8 Gy in 31 fractions with mitomycin and 5-Flurouracil from 2014 Dec. 15 to 2015 Feb. 10. The patient achieved a complete response to the treatment for 2 years. However, the patient developed grade 3 radiation proctitis with frequent bleeding in 2016 January. The symptoms were refractory to sulfasalazine and steroids enema treatment for 6 months. Anal biopsy reported chronic inflammation. The patient had been treated with sodium butyrate 80 mM and 1% metformin enema (100 mL) for 2 weeks, and no bleeding events were reported after 2 weeks of treatment. The patient has remained symptom-free.

Example 4

Effect of Metformin and Sodium Butyrate on Radiation Cystitis

A 75-year old male patient was diagnosed with prostatic urothelial carcinoma. He was treated with transurethral resection followed by the definitive CCRT 65Gy/32fx in May 2014. Disease progressed with pubic bone metastases and he received a second course of palliative RT to 40Gy/20fx in July 2015. Starting from May 2016, he suffered from persisting gross hematuria with a diagnosis of radiation cystitis after a serial examinations of CT scan, cystoscope biopsies. The symptoms were refractory to conventional treatment including steroids and anti-inflammatory drugs. In November 2016, the patient received intravesical douching with sodium butyrate 80 mM and 1% metformin solution (100 mL) through Foley catheter. Each treatment retained 30 minutes and was administered three times a week for a total of 10 cycles. He reported disappearance of gross hematuria after the third treatment. Urine analysis showed a significant decrease of red blood cells (RBCS) (from more than 100 to about 8-15) for the following 4 months.

Example 5

Effect of Metformin and Sodium Butyrate on Radiation Osteonecrosis

Two patients (on 69-year old and one 59-year old) suffered from buccal cancer. Both patients received the full dose of radiotherapy and chemotherapy as the primary treatment. They had history of tooth extraction before radiotherapy. Patients suffered from unhealed molar ulcer with severe pain at right mandible 2 and 3 months after the treatment. Symptoms were refractory to conventional dental debridement and antibiotics for more than 3 months. Then, both patients were treated with sodium butyrate 80 mM and 1% metformin solution (100 mL) on gauze applied at wound site twice daily for a total of 4 weeks. Both patients' symptoms significantly improved after one week of treatment, and the wound has healed after 2 and 3 weeks of treatment, respectively.

The clinical data provided in Example 3 to Example 5 demonstrated that the present treatment of metformin and sodium butyrate effectively ameliorate a variety of chronic conditions caused by the radiotherapy, such as radiation proctitis, radiation cystitis and radiation osteonecrosis.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating chronic inflammation caused by radiation in a subject in need thereof, comprising administering to the subject a therapeutically effective amount of a combination of metformin and sodium butyrate, wherein the combination has synergistic effect in treating chronic inflammation caused by radiation,
   wherein the chronic inflammation caused by radiation is refractory to steroids and sulfasalazine,
   and wherein the chronic inflammation caused by radiation is radiation proctitis, radiation proctosigmoiditis, radiation proctocolitis, radiation dermatitis, radiation cystitis, or radiation osteonecrosis.

2. The method of claim 1, wherein metformin is administered in the combination in an amount of 1 to 40 grams per day.

3. The method of claim 2, wherein metformin is administered in the combination in an amount of 1 to 10 grams per day.

4. The method of claim 2, wherein the metformin is administered to the subject once, twice or three times a day.

5. The method of claim 1, wherein sodium butyrate is administered in the combination in an amount of 0.1 to 4 grams per day.

6. The method of claim 5, wherein sodium butyrate is administered in the combination in an amount of 0.5 to 1 gram per day.

7. The method of claim 5, wherein the metformin and sodium butyrate are administered concurrently or independently to the subject once, twice or three times a day.

8. The method of claim 1, wherein the metformin and sodium butyrate are formulated in a single pharmaceutical composition.

9. The method of claim 1, wherein the metformin and sodium butyrate are formulated in two separate pharmaceutical compositions.

10. The method of claim 9, wherein the metformin and sodium butyrate are administered concurrently.

11. The method of claim 1, wherein the metformin and sodium butyrate are administered topically, rectally, enterally, or via injection, infusion or catheter delivery.

* * * * *